(12) United States Patent
Amasaki et al.

(10) Patent No.: US 7,897,761 B2
(45) Date of Patent: Mar. 1, 2011

(54) HETEROCYCLIC COMPOUND

(75) Inventors: Ichiro Amasaki, Odawara (JP); Naoyuki Hanaki, Minami-ashigara (JP)

(73) Assignee: Fujifilm Corporation, Minato-Ku, Tokyo (JP)

( * ) Notice: Subject to any disclaimer, the term of this patent is extended or adjusted under 35 U.S.C. 154(b) by 356 days.

(21) Appl. No.: 12/057,859

(22) Filed: Mar. 28, 2008

(65) Prior Publication Data

US 2010/0004439 A1 Jan. 7, 2010

(30) Foreign Application Priority Data

Mar. 30, 2007 (JP) ................................ 2007-095435
Jan. 31, 2008 (JP) ................................ 2008-021824

(51) Int. Cl.
*C07D 413/14* (2006.01)
(52) U.S. Cl. ........................................... 544/92; 544/90
(58) Field of Classification Search ...................... 544/92
See application file for complete search history.

(56) References Cited

FOREIGN PATENT DOCUMENTS

| JP | 62-11744 A | 1/1987 |
|----|-----------|--------|
| JP | 5-339033 A | 12/1993 |
| JP | 5-345639 A | 12/1993 |
| JP | 6-56466 | 3/1994 |
| JP | 6-145387 A | 5/1994 |
| JP | 7-285927 A | 10/1995 |
| JP | 2003-177235 A | 6/2003 |
| JP | 2005-517787 A | 6/2005 |
| WO | WO 03/070819 A1 | 8/2003 |

*Primary Examiner* — Kahsay T Habte
(74) *Attorney, Agent, or Firm* — Buchanan Ingersoll & Rooney PC

(57) ABSTRACT

A compound represented by the following Formula (1):

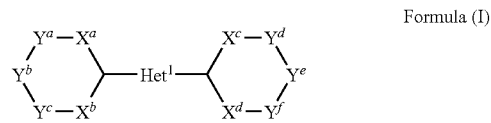

Formula (I)

wherein, $Het^1$ represents a bivalent five- or six-membered aromatic heterocyclic residue and may further be substituted; $X^a$ to $X^d$ each independently represent a heteroatom and may further be substituted; $Y^a$ to $Y^f$ each independently represent a heteroatom or a carbon atom and may further be substituted; the ring bound to $Het^1$ may have a double bond at any position.

2 Claims, No Drawings

HETEROCYCLIC COMPOUND

FIELD OF THE INVENTION

The present invention relates to a heterocyclic compound, and an ultraviolet absorbent and a fluorescent brightener of the compound.

BACKGROUND OF THE INVENTION

An ultraviolet absorbent has been used together with various resins, for providing the resins with ultraviolet absorptivity. Inorganic or organic ultraviolet absorbents are used as the ultraviolet absorbents. Inorganic ultraviolet absorbents (see, for example, JP-A-5-339033 ("JP-A" means unexamined published Japanese patent application), JP-A-5-345639, and JP-A-6-56466 and others) are superior in durability such as weather resistance and heat resistance, but the degree of freedom in selecting the compound is limited, because the absorption wavelength is determined by the band gap of the compound, and in addition, there is no inorganic absorbent capable to absorb the light in a long-wavelength ultraviolet (UV-A) range of around 400 nm, and even if there is an absorbent capable to absorb the light in the long-wavelength ultraviolet light, the absorbent develops color, because it has an absorption also in the visible range.

In contrast, the degree of freedom in designing structures is much higher for organic ultraviolet absorbents, and thus, it is possible to obtain an absorbent having a various absorption wavelength by designing the absorbent structure properly.

Various organic ultraviolet absorbent systems have been studied, and two ways of thinking, namely, use of an absorbent having the maximum absorption wavelength in the long-wavelength ultraviolet range and use of a high concentration of absorbent are considered for absorbing the light in the long-wavelength ultraviolet range. However, the absorbents disclosed in JP-A-6-145387 and JP-A-2003-177235 and others having the maximum absorption wavelength in the long-wavelength ultraviolet range were lower in light stability, and their absorption capacity declines over time.

In contrast, benzophenone- and benzotriazole-based ultraviolet absorbents are relatively higher in light stability, and increase in concentration or film thickness leads to relatively clear blocking of the light in the longer-wavelength range (see, for example, JP-A-7-2005-517787 and JP-A-7-285927 and others). Further, benzoxazinone-based ultraviolet absorbents are also known (see, for example, JP-A-62-11744). However, when such an ultraviolet absorbent is coated as it is mixed with a resin and others, the film thickness is normally at most about dozens of μm. In order to block the light in the longer-wavelength range by this film thickness, it is necessary to add the ultraviolet absorbent in a significantly higher concentration. However, a mere increase in concentration only resulted in a problem of precipitation and bleed out of the ultraviolet absorbent during long-term use. There are some ultraviolet absorbents that are irritative to skin and accumulate in the body among the benzophenone- and benzotriazole-based ultraviolet absorbents, and thus, intensive care should have been given to these compounds during use.

SUMMARY OF THE INVENTION

The present invention resides in a compound represented by the following Formula (1):

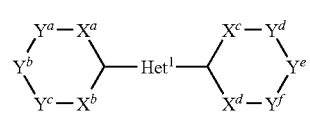

Formula (1)

wherein, $Het^1$ represents a bivalent five- or six-membered aromatic heterocyclic residue; the aromatic heterocyclic residue may further be substituted;

$X^a, X^b, X^c$ and $X^d$ each independently represent a heteroatom, $X^a$ to $X^d$ may further be substituted;

$Y^a, Y^b, Y^c, Y^d, Y^e$ and $Y^f$ each independently represent a heteroatom or a carbon atom;

$Y^a$ to $Y^f$ may further be substituted;

the ring bound to $Het^1$ may have a double bond at any position.

Further, the present invention resides in an ultraviolet absorbent comprising the compound described above.

Further, the present invention resides in a fluorescent brightener comprising the compound described above.

Other and further features and advantages of the invention will appear more fully from the following description.

DETAILED DESCRIPTION OF THE INVENTION

After studying intensively on heterocyclic compounds in detail, the inventors have found a compound that has a novel structure and is superior in light fastness and absorbs ultraviolet ray in the longer wavelength range that was hitherto impossible to be covered, and thus, made the present invention.

The present invention provides the following means.

<1> A compound represented by the following Formula (1):

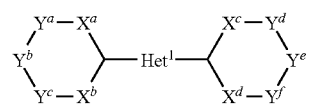

Formula (1)

wherein, $Het^1$ represents a bivalent five- or six-membered aromatic heterocyclic residue; the aromatic heterocyclic residue may further be substituted;

$X^a, X^b, X^c$ and $X^d$ each independently represent a heteroatom, $X^a$ to $X^d$ may further be substituted;

$Y^a, Y^b, Y^c, Y^d, Y^e$ and $Y^f$ each independently represent a heteroatom or a carbon atom;

$Y^a$ to $Y^f$ may further be substituted;

the ring bound to $Het^1$ may have a double bond at any position.

<2> The compound described in <1>, wherein at least one of the ring formed from $X^a, X^b, Y^a$ to $Y^c$ and carbon atom and the ring formed from $X^c, X^d, Y^d$ to $Y^f$ and carbon atom is a fused ring.

<3> The compound described in <1> or <2>, wherein at least one of the ring formed from $X^a, X^b, Y^a$ to $Y^c$ and carbon atom and the ring formed from $X^c, X^d, Y^d$ to $Y^f$ and carbon atom is not a perimidine ring.

<4> The compound described in any one of <1> to <3>, wherein the compound represented by Formula (1) above is a compound represented by the following Formula (2):

Formula (2)

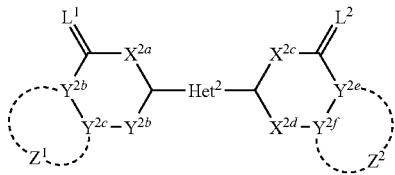

wherein, $Het^2$ is the same as $Het^1$ in Formula (1) above;
$X^{2a}, X^{2b}, X^{2c}$ and $X^{2d}$ each are the same as $X^a, X^b, X^c$ and $X^d$ in Formula (1) above;
$Y^{2b}, Y^{2c}, Y^{2e}$ and $Y^{2f}$ each are the same as $Y^b, Y^c, Y^e$ and $Y^f$ in Formula (1) above;
$L^1$ and $L^2$ each independently represent an oxygen atom or sulfur atom or $=NR^a$, where $R^a$ represents a hydrogen atom or a monovalent substituent group;
$Z^1$ and $Z^2$ each independently represent an atom group needed to form a four- to eight-membered ring together with $Y^{2b}$ and $Y^{2c}$ or $Y^{2e}$ and $Y^{2f}$.

<5> The compound described in <4>, wherein the compound represented by Formula (2) above is a compound represented by the following Formula (3):

Formula (3)

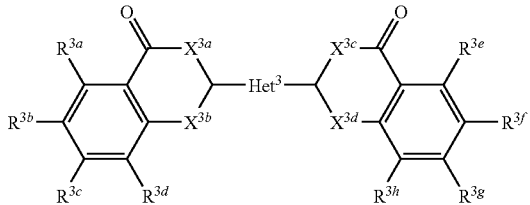

wherein, $Het^3$ is the same as $Het^2$ in Formula (2) above;
$X^{3a}, X^{3b}, X^{3c}$ and $X^{3d}$ each are the same as $X^{2a}, X^{2b}, X^{2c}$ and $X^{2d}$ in Formula (2) above;
$R^{3a}, R^{3b}, R^{3c}, R^{3d}, R^{3e}, R^{3f}, R^{3g}$ and $R^{3h}$ each independently represent a hydrogen atom or a monovalent substituent group.

<6> The compound described in <5>, wherein the compound represented by Formula (3) above is a compound represented by the following Formula (4):

Formula (4)

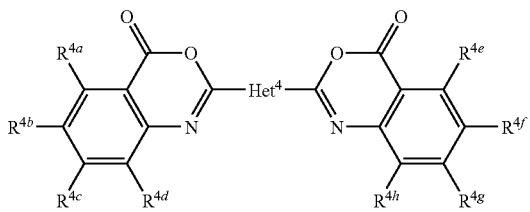

wherein, $Het^4$ is the same as $Het^3$ in Formula (3) above;
$R^{4a}, R^{4b}, R^{4c}, R^{4d}, R^{4f}, R^{4g}$ and $R^{4h}$ each are the same as $R^{3a}, R^{3b}, R^{3c}, R^{3d}, R^{3e}, R^{3f}, R^{3g}$ and $R^{3h}$ in Formula (3) above.

<7> The compound described in <6>, wherein the compound represented by Formula (4) above is a compound represented by the following Formula (5):

Formula (5)

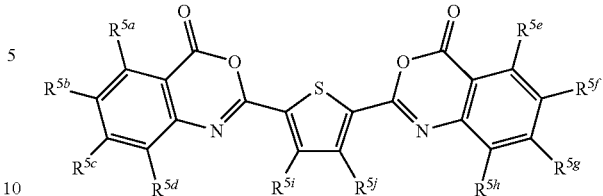

wherein, $R^{5a}, R^{5b}, R^{5c}, R^{5d}, R^{5e}, R^{5f}, R^{5g}$ and $R^{5h}$ each are the same as $R^{4a}, R^{4b}, R^{4c}, R^{4d}, R^{4e}, R^{4f}, R^{4g}$ and $R^{4h}$ in Formula (4) above; $R^{5i}$ and $R^{5j}$ each independently represent a hydrogen atom or a monovalent substituent group.

<8> An ultraviolet absorbent, comprising the compound described in any one of <1> to <7>.

<9> A fluorescent brightener, comprising the compound described in any one of <1> to <7>.

Hereinafter, the present invention will be described in detail.

In Formula (1) above, $Het^1$ represents a bivalent five- or six-membered aromatic heterocyclic residue having at least one hetero atom. $Het^1$ may be a fused ring.

Examples of the hetero atoms include boron, nitrogen, oxygen, silicon, phosphorus, sulfur, selenium, tellurium, and the like, preferably, nitrogen, oxygen and sulfur atoms, more preferably nitrogen and sulfur atoms, and particularly preferably a sulfur atom. If the ring has two or more hetero atoms, the hetero atoms may be the same as or different from each other.

Examples of the aromatic heterocycles prepared by adding two hydrogen atoms to a bivalent aromatic heterocyclic residue include pyrrole, pyrazole, imidazole, 1,2,3-triazole, 1,2,4-triazole, pyridine, pyridazine, pyrimidine, pyrazine, 1,3,5-triazine, furan, thiophene, oxazole, isoxazole, thiazole, isothiazole, 1,2,3-oxadiazole, 1,3,4-thiadiazole, and the like. The aromatic heterocycle is preferably pyrrole, pyridine, furan, or thiophene, more preferably pyridine or thiophene, and particularly preferably thiophene. The site of the aromatic heterocycle where the hydrogen atom is abstracted is arbitrary. For example, in the case of a five-membered heterocyclic compound pyrrole, the sites are for example, 2- and 3-sites, 2- and 4-sites, 2- and 5-sites, 3- and 4-sites, and 3- and 5-sites. Alternatively, in the case of a six-membered heterocyclic compound pyridine, the sites are 2- and 3-sites, 2- and 4-sites, 2- and 5-sites, 2- and 6-sites, 3- and 4-sites, 3- and 5-sites, and 3- and 6-sites.

The aromatic heterocyclic residue may have a substituent group(s). The substituent group is, for example, a monovalent substituent group. Examples of the monovalent substituent groups (hereinafter, referred to as R) include halogen atoms (e.g., fluorine atom, chlorine atom, bromine atom, and iodine atom), alkyl groups having 1 to 20 carbon atoms (e.g., methyl and ethyl), aryl groups having 6 to 20 carbon atoms (e.g., phenyl and naphthyl), a cyano group, a carboxyl group, alkoxycarbonyl groups (e.g., methoxycarbonyl), aryloxycarbonyl groups (e.g., phenoxycarbonyl), substituted or unsubstituted carbamoyl groups (e.g., carbamoyl, N-phenylcarbamoyl and N,N-dimethylcarbamoyl), alkylcarbonyl groups (e.g., acetyl), arylcarbonyl groups (e.g., benzoyl), a nitro group, substituted or unsubstituted amino groups (e.g., amino, dimethylamino and anilino), acylamino groups (e.g., acetamido and ethoxycarbonylamino), sulfonamido groups (e.g., methane sulfonamide), imido groups (e.g., succinimido and phthalimido), imino groups (e.g., benzylideneamino), a hydroxy group, alkoxy groups having 1 to 20 carbon atoms (e.g., methoxy), aryloxy groups (e.g., phenoxy), acyloxy groups (e.g., acetoxy), alkylsulfonyloxy groups (e.g., methanesulfonyloxy), arylsulfonyloxy groups (e.g., benzenesulfonyloxy), a sulfo group, substituted or unsubstituted sulfamoyl groups (e.g., sulfamoyl and N-phenylsulfamoyl), alkylthio groups (e.g., methylthio), arylthio groups (e.g., phenylthio), alkylsulfonyl groups (e.g., methanesulfonyl), arylsulfonyl groups (e.g., benzenesulfonyl), heterocyclic groups having 6 to 20 carbon atoms (e.g., pyridyl, morpholino), and the like. The substituent group may be further substituted, and the multiple substituent groups, if present, may be the same as or different from each other. The substituent groups then are, for example, the monovalent substituents R described above. The substituent groups may bind to each other to form a ring.

The substituent group is preferably an alkyl group, an alkoxy group, or an aryl group, more preferably an alkyl or aryl group, and particularly preferably an alkyl group.

$X^a$, $X^b$, $X^c$ and $X^d$ each independently represent a heteroatom. Examples of the hetero atoms include boron, nitrogen, oxygen, silicon, phosphorus, sulfur, selenium, tellurium, and the like, preferably, nitrogen, oxygen and sulfur atoms, more preferably nitrogen and oxygen atoms. $X^a$ to $X^d$ may have a substituent group(s). The substituent groups then are, for example, the monovalent substituents R described above.

$Y^a$, $Y^b$, $Y^c$, $Y^d$, $Y^e$ and $Y^f$ each independently represent a heteroatom or a carbon atom. The atoms constituting $Y^a$ to $Y^f$ include, for example, carbon atom, nitrogen atom, oxygen atom, sulfur atom and the like. The atoms constituting $Y^a$ to $Y^f$ are preferably carbon atom, nitrogen atom, and oxygen atom, more preferably carbon atom and nitrogen atom, still more preferably carbon atom, and particularly preferably all carbon atoms. The atom may further be substituted, and the substituent groups may bind to each other to form a ring, which may additionally be fused with another ring. The substituent groups then are, for example, the monovalent substituents R described above.

At least one of the ring formed from $X^a$, $X^b$, $Y^a$ to $Y^c$ and carbon atom and the ring formed from $X^c$, $X^d$, $Y^d$ to $Y^f$ and carbon atom (two rings bound to the aromatic heterocyclic residue represented by $Het^1$) preferably has a fused ring. In addition, at least one of the two rings is preferably not a perimidine ring Specific examples of the compounds are shown in the following Tables 1 to 6, as the ring formed from $X^a$, $X^b$, $Y^a$ to $Y^c$ and carbon atom is designated as A, the aromatic heterocyclic residue represented by $Het^1$ as Het, and the ring formed from $X^c$, $X^d$, $Y^d$ to $Y^f$ and carbon atom as B.

TABLE 2-continued

| A | Het | B |
|---|-----|---|
| (benzothiazine with NMe, S, Me, N) | 2,5-dimethylfuran with Ph | (benzothiazine with NMe, S, Me, N) |
| (benzothiazine with S, S, Me, N) | 2,5-disubstituted furan (Et) | (benzothiazine with S, S, Me, N) |
| (pyrazino-oxazinone) | tetramethylfuran | (pyrazino-oxazinone) |
| (pyrido-oxazinone) | 3,4-dimethylfuran-OH | (pyrido-oxazinone) |
| (thieno-oxazinone) | 3,5-dimethylpyrazole | (thieno-oxazinone) |
| (pyrrolo-oxazinone) | 2,5-dimethylimidazole | (pyrrolo-oxazinone) |

TABLE 3

| A | Het | B |
|---|-----|---|
| (furo-oxazinone) | 4,5-dimethyltriazole | (furo-oxazinone) |
| (6-methylbenzoxazinone) | 2,5-dimethylthiadiazole | (6-methylbenzoxazinone) |
| (6-hydroxybenzoxazinone) | 2,5-dimethylthiazole | (6-hydroxybenzoxazinone) |
| (7-chlorobenzoxazinone) | 3,5-dimethyl-1,2,4-triazole | (7-chlorobenzoxazinone) |
| (6,7-dimethoxybenzoxazinone) | 2,5-dimethylimidazole | (6,7-dimethoxybenzoxazinone) |
| (6-octyloxybenzoxazinone, $C_8H_{17}O$) | 2,5-dimethyloxazole | (6-octyloxybenzoxazinone, $C_8H_{17}O$) |

TABLE 3-continued
| A | Het | B |
|---|---|---|
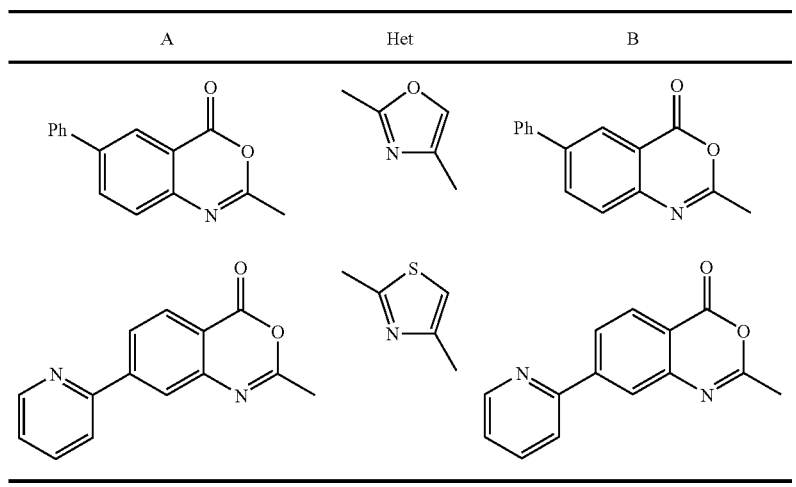
TABLE 4
| A | Het | B |
|---|---|---|
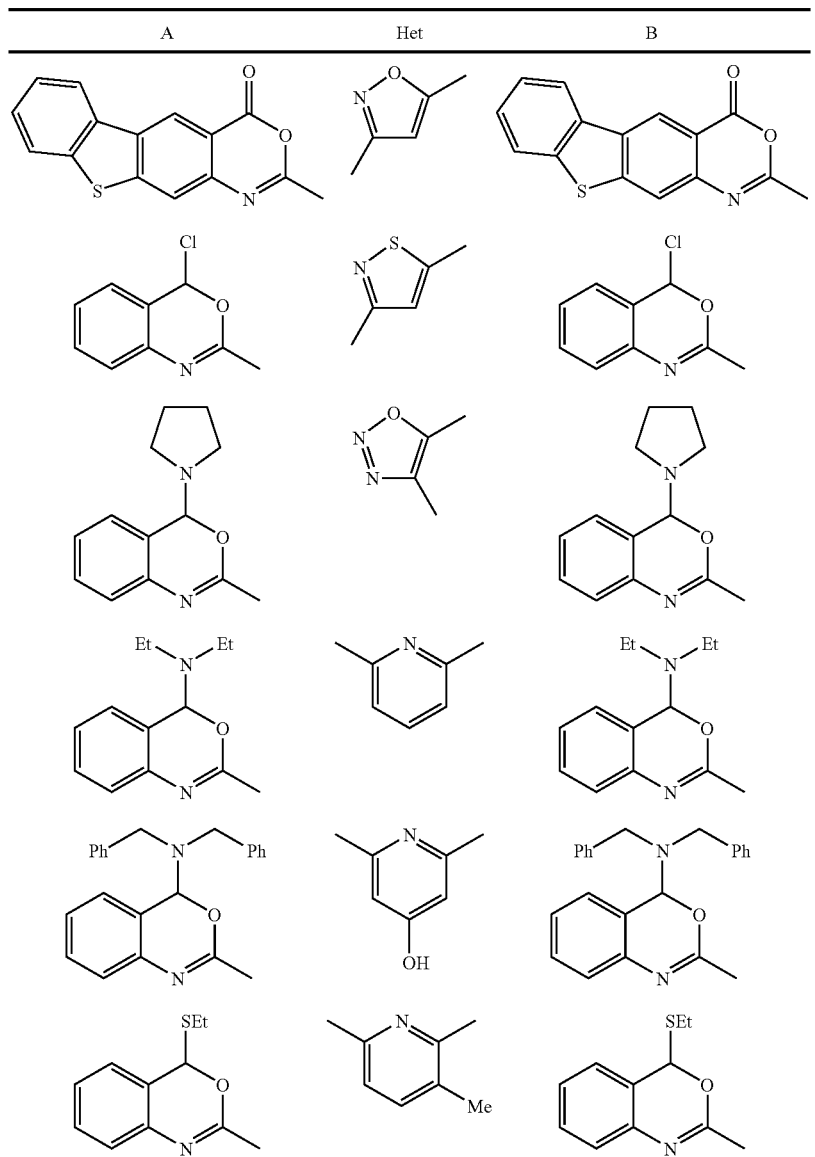

TABLE 4-continued
| A | Het | B |
|---|-----|---|
| 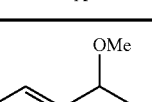 | 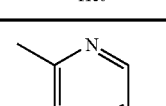 | 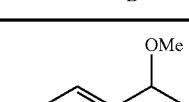 |
| 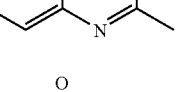 | 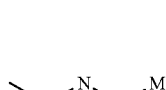 | 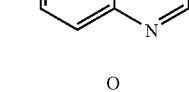 |
TABLE 5
| A | Het | B |
|---|-----|---|
| 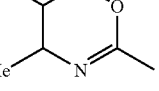 | 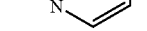 | 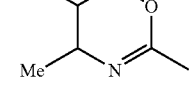 |
| 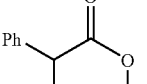 | 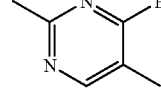 | 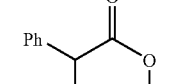 |
| 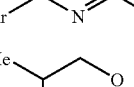 | 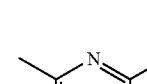 | 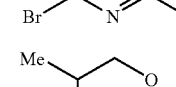 |
| 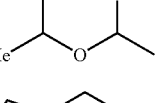 | 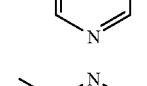 | 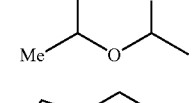 |
| 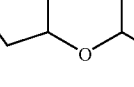 | 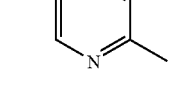 | 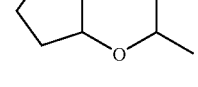 |
| 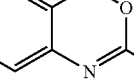 | 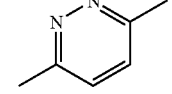 | 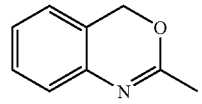 |
| 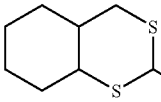 | 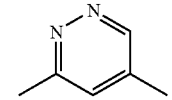 | 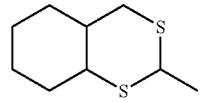 |
| 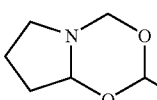 | 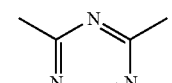 | 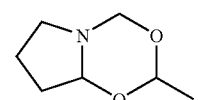 |

TABLE 6

| A | Het | B |
|---|-----|---|

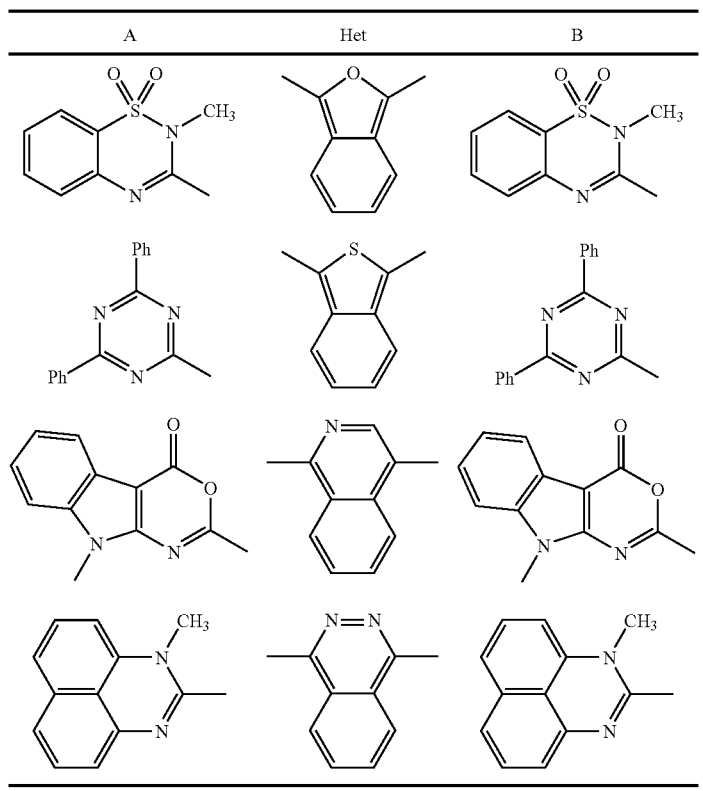

Hereinafter, specific examples of the rings formed from $X^a$, $X^b$, $Y^a$ to $Y^c$ and carbon atom and the rings formed from $X^c$, $X^d$, $Y^d$ to $Y^f$ and carbon atom (two rings bound to the aromatic heterocyclic residue represented by Het$^1$) are listed: wherein, (Z) represents the site bound to the aromatic heterocyclic residue represented by Het$^1$.

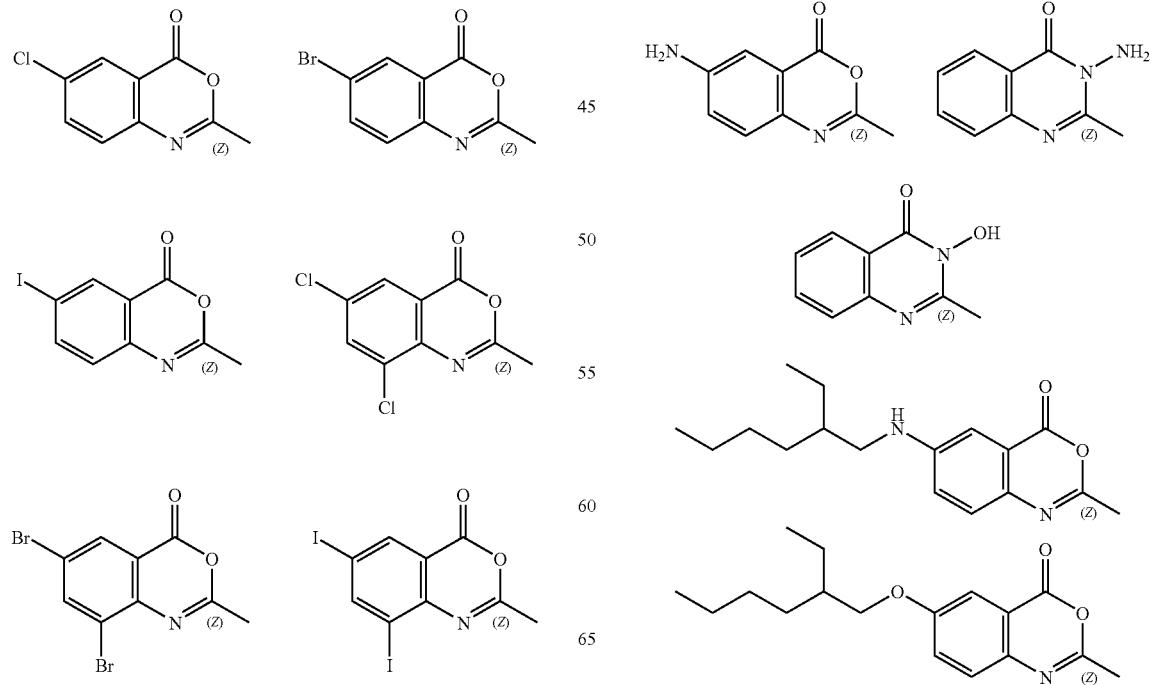

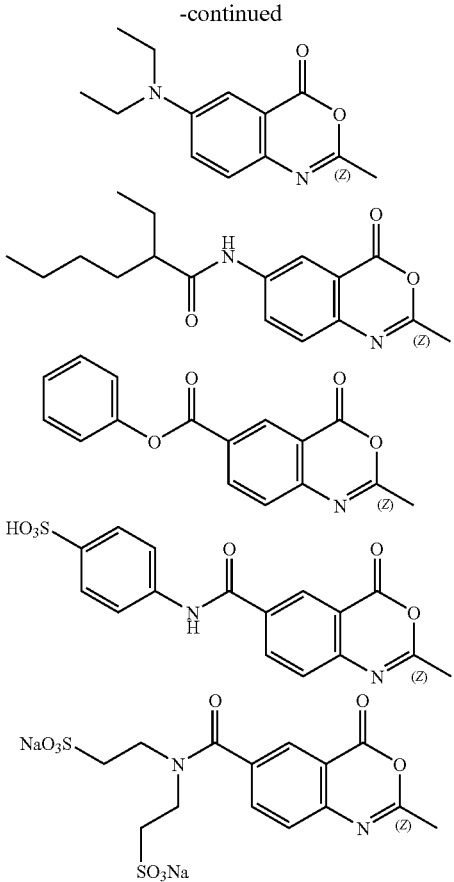

The compound represented by Formula (1) is preferably a compound represented by Formula (2) above. Hereinafter, the compound represented by the Formula (2) above will be described in detail.

Het$^2$ is the same as Het$^1$ in Formula (1) above and the favorable examples thereof are also the same.

$X^{2a}$, $X^{2b}$, $X^{2c}$ and $X^{2d}$ is the same as $X^a$, $X^b$, $X^c$ and $X^d$ in Formula (1) above and the favorable examples thereof are also the same. $X^{2a}$, $X^{2b}$, $X^{2c}$ and $X^{2d}$ may be the same as or different from each other. The combinations of $X^{2a}/X^{2b}$ and $X^{2c}/X^{2d}$ are more preferably respectively the same as each other, and particularly preferably, $X^{2a}$ and $X^{2c}$ are oxygen atoms and $X^{2b}$ and $X^{2d}$ are nitrogen atoms.

$Y^{2b}$, $Y^{2c}$, $Y^{2e}$ and $Y^{2f}$ each are the same as $Y^b$, $Y^c$, $Y^e$ and $Y^f$ in Formula (1) above and the favorable examples thereof are also the same.

$L^1$ and $L^2$ each independently represent an oxygen atom or sulfur atom or $=NR^a$ ($R^a$ represents a hydrogen atom or a monovalent substituent group. The substituent group is, for example, the monovalent substituent R described above), preferably an oxygen atom or $=NR^a$. It is more preferably an oxygen atom. $L^1$ and $L^2$ may be the same as or different from each other, but preferably the same. In particular, $L^1$ and $L^2$ are particularly favorably both oxygen atoms.

$Z^1$ and $Z^2$ each independently represent an atom group needed for forming a four- to eight-membered ring together with $Y^{2b}$ and $Y^{2c}$, or $Y^{2e}$ and $Y^{2f}$. These rings may have a substituent group(s), which may further have a fused ring. Examples of the rings formed include aliphatic hydrocarbon rings such as cyclohexane and cyclopentane; aromatic hydrocarbon rings such as benzene and naphthalene; and heterocycles such as pyridine, pyrrole, pyridazine, thiophene, imidazole, furan, pyrazole, oxazole, triazole, thiazole, or the benzo-fused rings thereof, and the like. Preferable are aromatic hydrocarbon rings and heterocycles. More preferable are aromatic hydrocarbon rings, and particularly preferable is a benzene ring.

Further, the compound represented by Formula (2) is preferably a compound represented by Formula (3) above. Hereinafter, the compound represented by the Formula (3) above will be described in detail.

Het$^3$ is the same as Het$^2$ in Formula (2) above and the favorable examples thereof are also the same.

$X^{3a}$, $X^{3b}$, $X^{3c}$ and $X^{3d}$ each are the same as $X^{2a}$, $X^{2b}$, $X^{2c}$ and $X^{2d}$ in Formula (2) above and the favorable examples thereof are also the same. $X^{3a}$, $X^{3b}$, $X^{3c}$ and $X^{3d}$ may be the same as or different from each other. The combinations of $X^{3a}/X^{3b}$ and $X^{3c}/X^{3d}$ are more preferably respectively the same as each other, and particularly preferably, $X^{3a}$ and $X^{3c}$ are oxygen atoms and $X^{3b}$ and $X^{3d}$ are nitrogen atoms.

$R^{3a}$, $R^{3b}$, $R^{3c}$, $R^{3d}$, $R^{3e}$, $R^{3f}$, $R^{3g}$ and $R^{3h}$ each independently represent a hydrogen atom or a monovalent substituent group. The substituent groups then are, for example, the monovalent substituents R described above.

Any two substituent groups among $R^{3a}$ to $R^{3d}$ and $R^{3e}$ to $R^{3h}$ may bind to each other to form a ring, which may have additionally a fused ring. $R^{3a}$ to $R^{3h}$ each preferably represent a hydrogen atom, an alkyl group having 10 or less carbon atoms, an alkoxy group having 10 or less carbon atoms, or a hydroxy group, more preferably a hydrogen atom or an alkoxy group having 10 or less carbon atoms, still more preferably a hydrogen atom, and particularly preferably, $R^{3a}$ to $R^{3h}$ are all hydrogen atoms.

Further, the compound represented by Formula (3) is preferably a compound represented by Formula (4) above. Hereinafter, the compound represented by the Formula (4) above will be described in detail.

Het$^4$ is the same as Het$^3$ in Formula (3) above and the favorable examples thereof are also the same.

$R^{4a}$, $R^{4b}$, $R^{4c}$, $R^{4d}$, $R^{4e}$, $R^{4f}$, $R^{4g}$ and $R^{4h}$ each are the same as $R^{3a}$, $R^{3b}$, $R^{3c}$, $R^{3d}$, $R^{3e}$, $R^{3f}$, $R^{3g}$ and $R^{3h}$ in Formula (3) above and the favorable examples thereof are also the same.

Further, the compound represented by Formula (4) is preferably a compound represented by Formula (5) above. Hereinafter, the compound represented by the Formula (5) above will be described in detail.

Het$^5$ is the same as Het$^4$ in Formula (4) above and the favorable examples thereof are also the same.

$R^{5a}$, $R^{5b}$, $R^{5c}$, $R^{5d}$, $R^{5e}$, $R^{5f}$, $R^{5g}$ and $R^{5h}$ each are the same as $R^{4a}$, $R^{4b}$, $R^{4c}$, $R^{4d}$, $R^{4e}$, $R^{4f}$, $R^{4g}$ and $R^{4h}$ in Formula (4) above and the favorable examples thereof are also the same. $R^{5i}$ and $R^{5j}$ each independently represent a hydrogen atom or a monovalent substituent group. The substituent groups then are, for example, the monovalent substituents R described above. $R^{5i}$ and $R^{5j}$ may bind to each other to form a ring, which may have additionally a fused ring. $R^{5i}$ and $R^{5j}$ each preferably represent a hydrogen atom, an alkyl group having 10 or less carbon atoms, an alkoxy group having 10 or less carbon atoms, or a hydroxy group, more preferably a hydrogen atom or an alkoxy group having 10 or less carbon atoms, still more preferably a hydrogen atom, and particularly preferably, $R^{5i}$ and $R^{5j}$ are both hydrogen atoms.

The compound represented by any one of Formulae (1) to (5) may be prepared by any method. Examples of the methods include those disclosed in known patent documents and non-patent documents, specifically those described in the Examples of JP-A-2000-264879, p. 4. left line 43 to right line 8; in the Examples of JP-A-2003-155375, p. 4, right column lines 5 to 30; "Bioorganic & Medicinal Chemistry", 2000, vol. 8, p. 2095-2103, "Bioorganic & Medicinal Chemistry Letters", 2003, vol. 13, p. 4077-4080, and others. For example, exemplary compound (15) can be prepared in reaction of 3,5-pyrazole dicarbonyl dichloride with anthranilic acid. Alternatively, exemplary compound (32) can be prepared in reaction of 2,5-thiophenedicarbonyl dichloride with 4,5-dimethoxyanthranilic acid.

Hereinafter, specific examples of the compounds represented by any one of Formulae (1) to (5) will be described below, but the present invention is not restricted thereby.

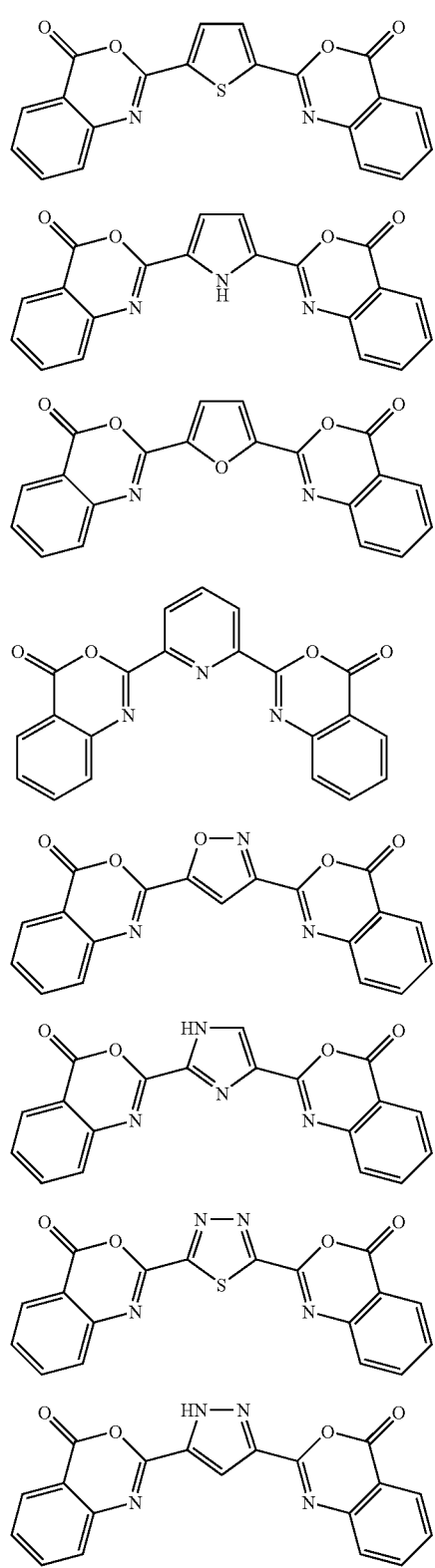
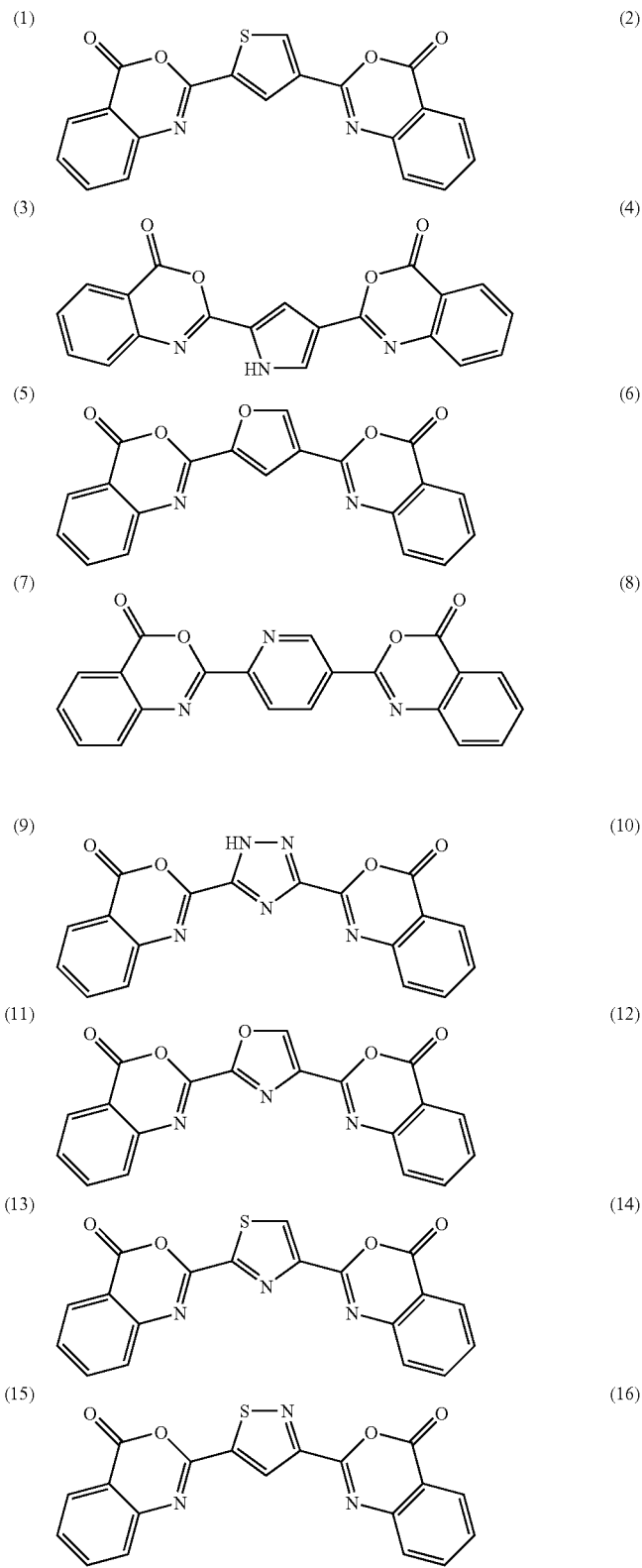

-continued
(17)
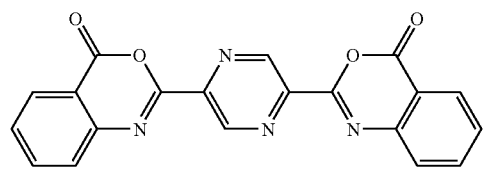
(18)
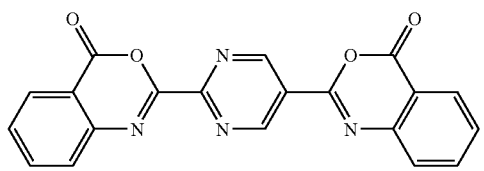
(19)
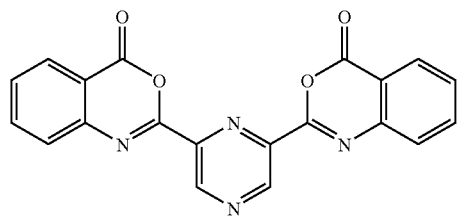
(20)
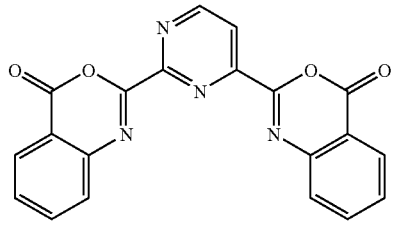
(21)
(22)
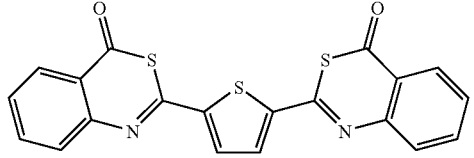
(23)
(24)
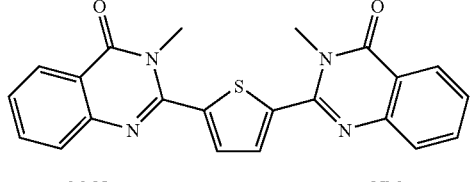
(25)
(26)
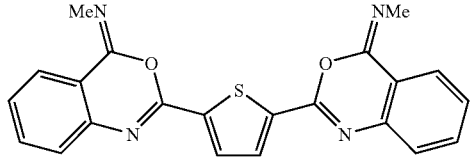
(27)
(28)
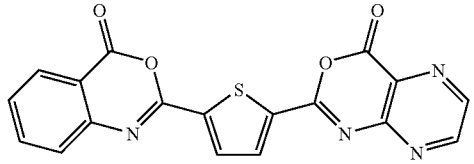
(29)
(30)
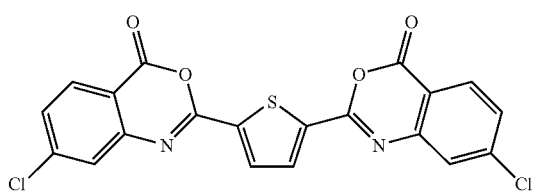
(31)
(32)
(33)
(34)
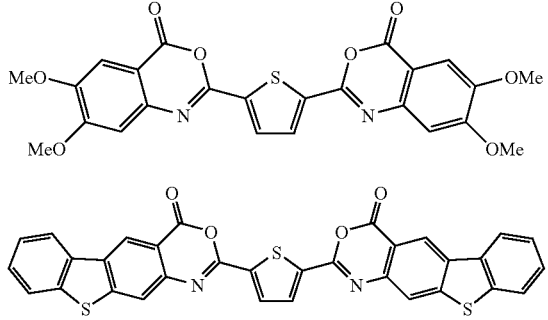

-continued
(35) 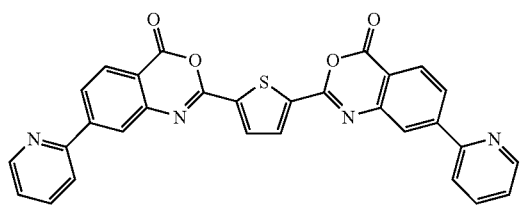
(36) 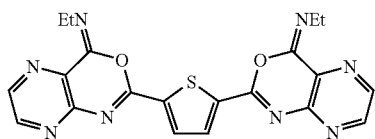
(37) 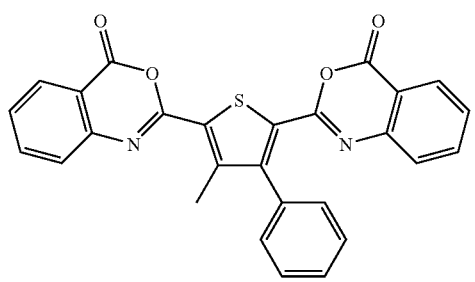
(38) 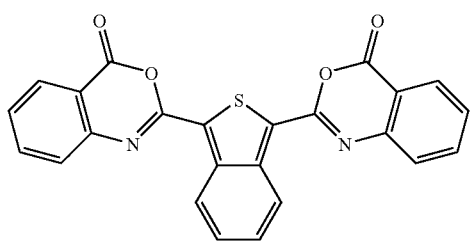
(39) 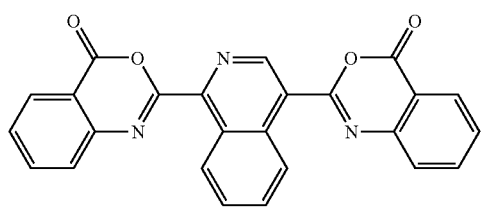
(40) 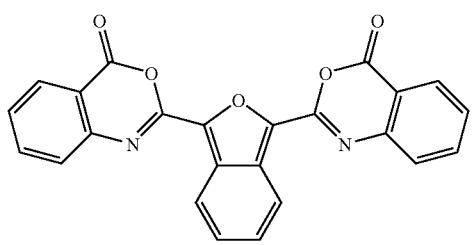
(41) 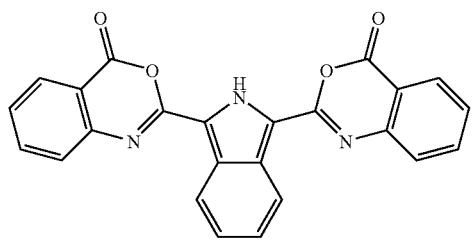
(42) 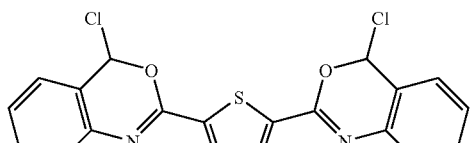
(43) 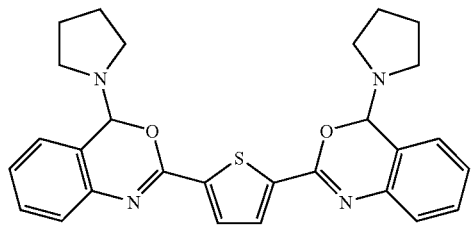
(44) 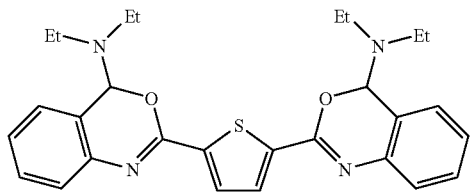
(45) 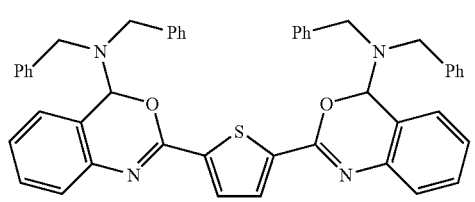
(46) 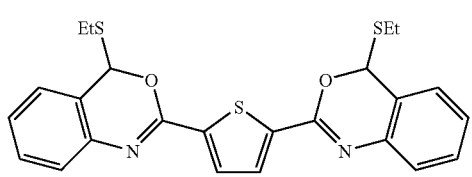
(47) 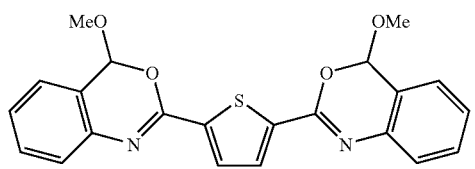
(48) 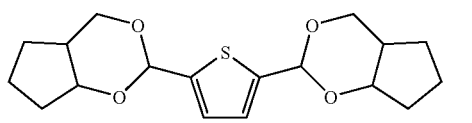

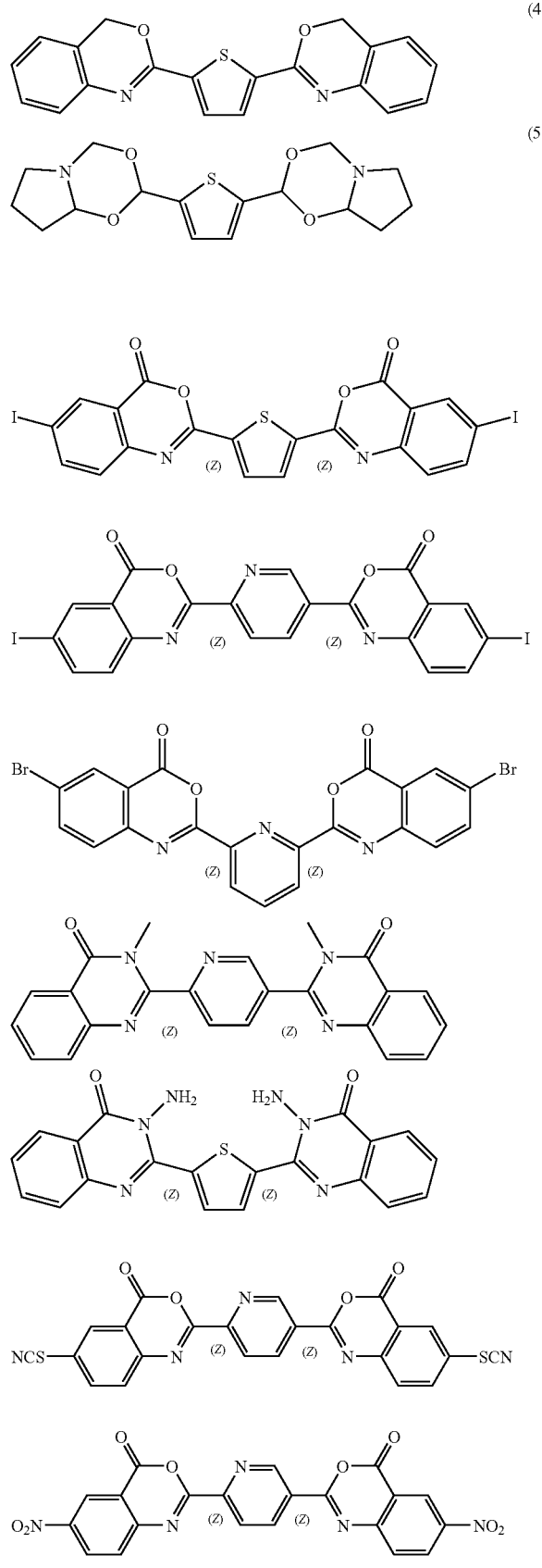
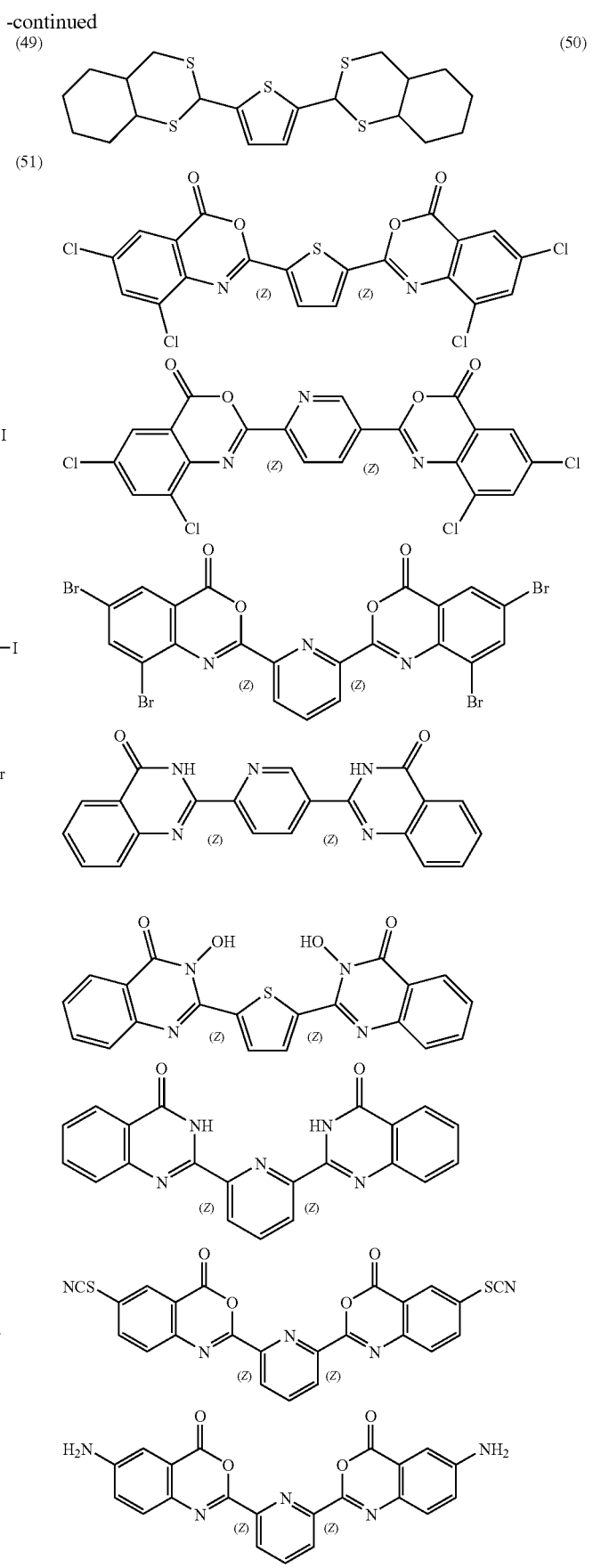

25
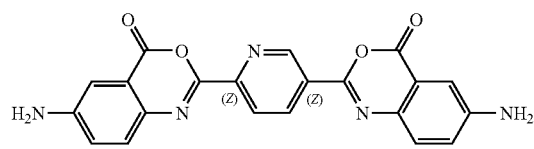
26
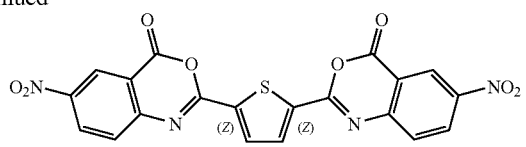
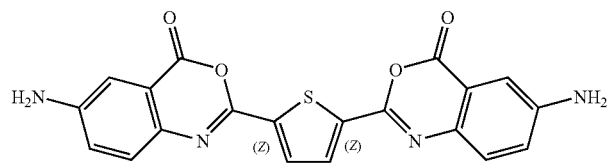
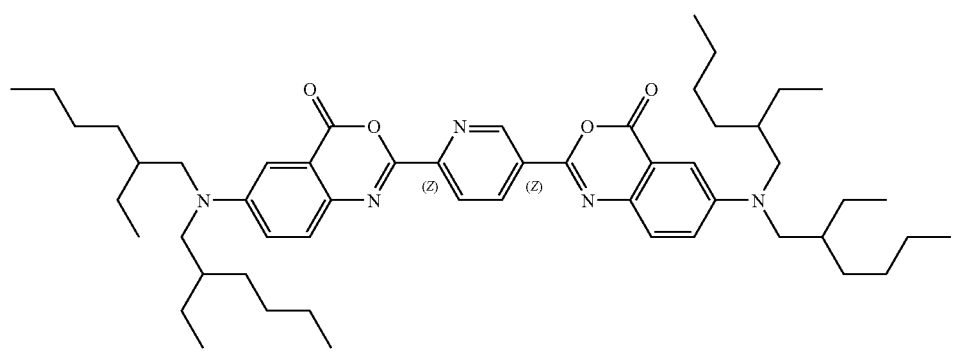
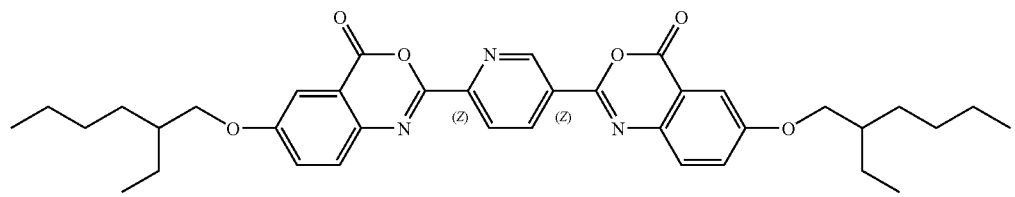
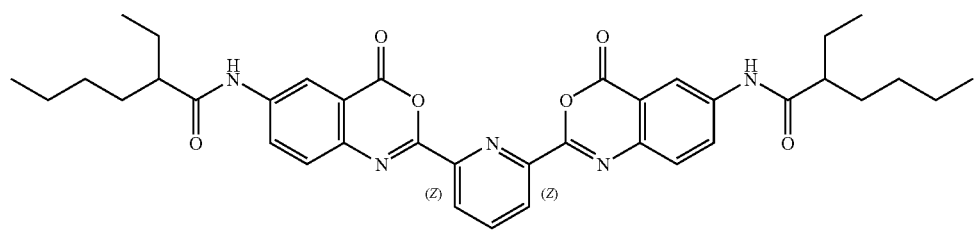
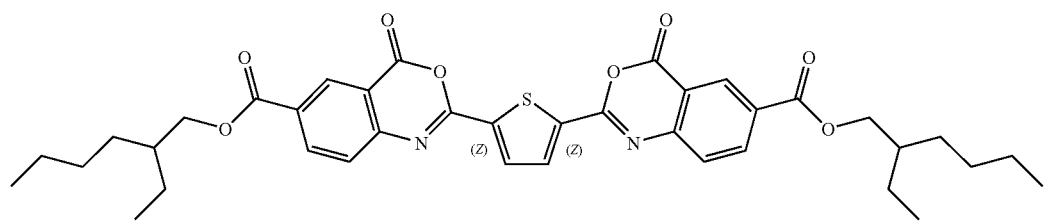
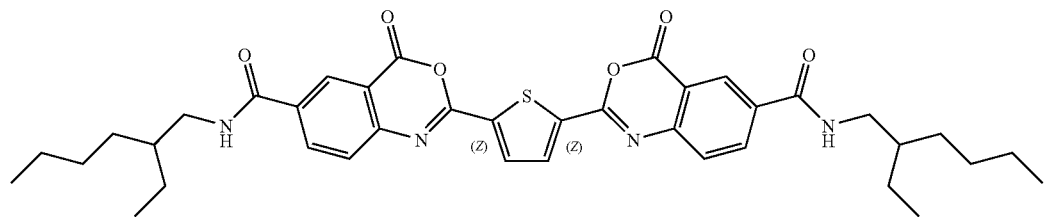

-continued

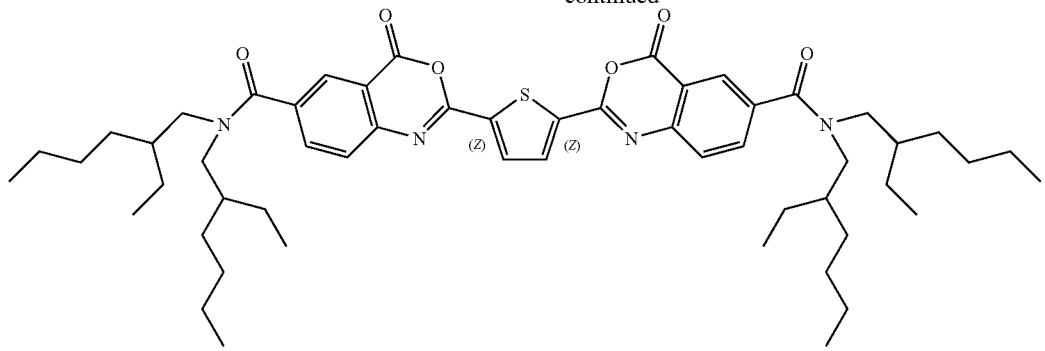

The compound according to the present invention may have tautomers depending on the structure and the environment where the compound is located. A typical form thereof is described here in the present invention, but the tautomers different from that described in the present invention are also included in the compound according to the present invention.

The compound according to the present invention may have an isotopic element (such as $^2$H, $^3$H, $^{13}$C, $^{15}$N, $^{17}$O, or $^{18}$O).

A polymer having the structure of the compound represented by Formulae (1) to (5) above in its recurring unit can also be used favorably in the present invention. The polymer may be a homopolymer having a single recurring unit or a copolymer having two or more kinds of recurring units. It may be a copolymer having another recurring unit additionally. Examples of the polymers having an ultraviolet absorbent structure in the recurring unit are described, for example, in each bulletin of JP-B-1-53455 ("JP-B" means examined Japanese patent publication) and JP-A-61-189530 and the specification of EP Patent No. 27242. The polymer can be prepared with reference to the methods described in these patent documents.

The compound represented by any one of Formulae (1) to (5) can be used favorably as an ultraviolet absorbent. Hereinafter, the compound represented by any one of Formulae (1) to (5) will be described when it is used as an ultraviolet absorbent.

The ultraviolet absorbent according to the present invention may be in any type of usage, for example, liquid dispersion, solution, polymer material, or the like.

The ultraviolet absorbent comprising the compound represented by any one of Formulae (1) to (5) above in the present invention can be used in the dispersed state as dispersed in a dispersed medium. Hereinafter, the ultraviolet absorbent dispersion including the ultraviolet absorbent according to the present invention will be described.

The medium for dispersing the ultraviolet absorbent according to the present invention is arbitrary. Examples thereof include water, organic solvents, resins, resin solutions, and the like. These media may be used alone or in combination of two or more.

Examples of the organic solvents as the dispersed medium for use in the present invention include hydrocarbon-based solvents such as pentane, hexane, and octane; aromatic solvents such as benzene, toluene, and xylene; ether-based solvents such as diethylether and methyl-t-butylether; alcoholic solvents such as methanol, ethanol, and isopropanol; ester-based solvents such as acetone, ethyl acetate and butyl acetate; ketone-based solvents such as methyl ethyl ketone; nitrile-based solvents such as acetonitrile and propionitrile; amide-based solvents such as N,N-dimethylformamide, N,N-dimethylacetamide, and N-methylpyrrolidone; sulfoxide-based solvents such as dimethylsulfoxide; amine-based solvents such as triethylamine and tributylamine; carboxylic acid-based solvents such as acetic acid and propionic acid; halogen-based solvents such as methylene chloride and chloroform; heteroring-based solvents such as tetrahydrofuran and pyridine; and the like. These solvents may be used as a mixture at any rate.

Examples of the resins as the dispersed medium for use in the present invention include various known thermoplastic and thermosetting resins commonly used for production of molded article, sheet, film and others. Examples of the thermoplastic resins include polyethylene series resins, polypropylene series resins, poly(meth)acrylic ester series resins, polystyrene series resins, styrene-acrylonitrile series resins, acrylonitrile-butadiene-styrene series resins, polyvinyl chloride series resins, polyvinylidene chloride series resins, polyvinyl acetate series resins, polyvinylbutyral series resins, ethylene-vinyl acetate series copolymers, ethylene-vinylalcohol series resins, polyethylene terephthalate resins (PET), polybutylene terephthalate resins (PBT), liquid crystal polyester resins (LCP), polyacetal resins (POM), polyamide resins (PA), polycarbonate resins, polyurethane resins, polyphenylene sulfide resins (PPS) and the like, and these resins may be used alone or as polymer blend or alloy of two or more.

The resin may be used as a thermoplastic molding material containing a natural resin and additionally filler such as glass fiber, carbon fiber, semi-carbonized fiber, cellulosic fiber or glass bead, a flame retardant, and the like. As needed, resin additives traditionally used, such as polyolefin series resin fine powder, polyolefin series wax, ethylene bisamide wax, and metal soap, may be used alone or in combination.

Examples of the thermosetting resins include epoxy resins, melamine resins, unsaturated polyester resins, and the like, and the resin may be used as a thermosetting molding material containing a natural resin and additionally filler, such as glass fiber, carbon fiber, semi-carbonized fiber or cellulosic fiber or glass bead, and a flame retardant.

The ultraviolet absorbent dispersion according to the present invention may contain other additives such as dispersant, antifoam, preservative, antifreezing agent, surfactant, and others. The dispersion may contain any other compounds additionally. Examples of the other additives include dye, pigment, infrared absorbent, flavoring agent, polymerizable compound, polymer, inorganic material, metal and the like.

For example, a high-shearing force high-speed-agitation dispersing machine or a high-strength ultrasonic dispersing machine may be used as the apparatus for preparation of the ultraviolet absorbent dispersion according to the present invention. Specific examples thereof include colloid mill, homogenizer, capillary emulsifier, liquid siren, electromagnetic-distortion ultrasonic wave generator, emulsifier having a Pallmann whistle, and the like. The high-speed-agitation dispersing machine favorably used in the present invention is a dispersing machine in which a dispersing part is revolving in solution at high speed (500 to 15,000 rpm, preferably 2,000 to 4,000 rpm) such as dissolver, polytron, homomixer, homoblender, keddy mill, or jet agitator. The high-speed-agitation dispersing machine for use in the present invention is also called a dissolver or a high-speed impeller dispersing machine, and, as described in JP-A-55-129136, a dispersing machine having impellers of saw-teeth shaped plate alternately bent in the vertical direction that are connected to the shaft revolving at high speed is also a favorable example.

Various methods may be used in preparation of an emulsified dispersion containing a hydrophobic compound. For example, in dissolving a hydrophobic compound in an organic solvent, the hydrophobic compound is dissolved in a solvent or a mixture of two or more selected from high-boiling point organic materials, water-immiscible low boiling point organic solvents and water-miscible organic solvents, and the solution is then dispersed in water or an aqueous hydrophilic colloid solution in the presence of a surfactant compound. The water-insoluble phase containing the hydrophobic compound and the aqueous phase may be mixed by the so-called normal mixing method of adding the water-insoluble phase into the agitated aqueous phase or by the reverse mixing method of adding the phases reversely.

The ultraviolet absorbent according to the present invention is favorably used in the state of a solution dissolved in a liquid medium. Hereinafter, the ultraviolet absorbent solution according to the present invention will be described.

The liquid dissolving the ultraviolet absorbent according to the present invention is arbitrary. It is, for example, water, an organic solvent, a resin, a resin solution, or the like. Examples of the organic solvent, the resin, and the resin solution include those described above as the dispersed medium. These may be used alone or in combination.

The solution of the ultraviolet absorbent according to the present invention may contain any other compounds additionally. Examples of the other additives include dye, pigment, infrared absorbent, flavoring agent, polymerizable compound, polymer, inorganic material, metal and the like. Components other than the ultraviolet absorbent according to the present invention may not necessarily be dissolved.

The content of the ultraviolet absorbent in the ultraviolet absorbent solution according to the present invention may not be determined specifically, because it varies according to application and type of usage, and thus the concentration is arbitrary according to application. The concentration in the entire solution is preferably 0.001 to 30 mass %, more preferably 0.01 to 10 mass %. A solution at higher concentration may be prepared and diluted at a desired time before use. The dilution solvent is selected arbitrarily from the solvents described above.

In the preparation of the polymer material containing the ultraviolet absorbent according to the present invention, the composition of the polymer substance is used. The composition of the polymer substance according to the present invention comprises the polymer substance described bellow and the ultraviolet absorbent according to the present invention contained therein.

The ultraviolet absorbent according to the present invention may be contained in the polymer substance in various methods. If the ultraviolet absorbent according to the present invention is compatible with the polymer substance, the ultraviolet absorbent according to the present invention may be added to the polymer substance directly. The ultraviolet absorbent according to the present invention may be dissolved in a cosolvent compatible with the polymer substance, and then the solution be added to the polymer substance. The ultraviolet absorbent according to the present invention may be dispersed in a high-boiling point organic solvent or a polymer, and the dispersion be added to the polymer substance.

The boiling point of high-boiling point organic solvent is preferably 180° C. or higher, more preferably 200° C. or higher. The melting point of the high-boiling point organic solvent is preferably 150° C. or lower, more preferably 100° C. or lower.

Examples of the high-boiling point organic solvents include phosphoric esters, phosphonic esters, benzoic esters, phthalic esters, fatty acid esters, carbonate esters, amides, ethers, halogenated hydrocarbons, alcohols and paraffins. Phosphoric esters, phosphonic esters, phthalic ester, benzoic esters and fatty acid esters are preferable.

The method of adding the ultraviolet absorbent according to the present invention is determined, by reference to the description in JP-A-58-209735, JP-A-63-264748, JP-A-4-191851, and JP-A-8-272058, and British Patent No. 2016017A.

The content of the ultraviolet absorbent according to the present invention in the ultraviolet absorbent solution is not determined specifically, because it varies according to application and type of usage, and the concentration is arbitrary according to desirable application. It is preferably 0.001 to 10 mass %, more preferably 0.01 to 5 mass %, in the polymer material.

The ultraviolet absorbent according to the present invention is used favorably in a polymer material. Hereinafter, the polymer material for use in the present invention will be described.

Although practically sufficient ultraviolet-shielding effect is obtained only with the ultraviolet absorbent according to the present invention, in the present invention, a white pigment which has higher hiding power, such as titanium oxide, may be used for assurance. In addition, a trace (0.05 mass % or less) amount of colorant may be used together, if the appearance or the color tone is of a problem or according to taste. Alternatively, a fluorescent brightener may be used together for applications demanding transparency or whiteness. Examples of the fluorescent brighteners include commercialized products, the compounds represented by Formula [1] and specific exemplary compounds 1 to 35 described in JP-A-2002-53824, and the like.

Subsequently, the polymer substance for use in the present invention will be described. The polymer substance may be a natural or synthetic polymer. Examples thereof include polyolefins (such as polyethylene, polypropylene, polyisobutylene, poly(1-butene), poly4-methylpentene, polyvinylcyclohexane, polystyrene, poly(p-methylstyrene), poly(α-methylstyrene), polyisoprene, polybutadiene, polycyclopentene, and polynorbornene); copolymers of a vinyl monomer (such as ethylene/propylene copolymer, ethylene/methylpentene copolymer, ethylene/heptene copolymer, ethylene/vinylcyclohexane copolymer, ethylene/cycloolefin copolymer (e.g., cycloolefin copolymer such as ethylene/norbornene), propylene/butadiene copolymer, isobutylene/isoprene copolymer, ethylene/vinylcyclohexene copolymer, ethylene/alkyl acrylate copolymer, and ethylene/alkyl methacrylate copolymer); acrylic polymers (such as polymethacrylate, polyacrylate, polyacrylamide, and polyacrylonitrile); polyvinyl chloride, polyvinylidene chloride, polyvinyl fluoride, polyvinylidene fluoride, vinyl chloride/vinyl acetate copolymer, polyethers (such as polyalkylene glycol, polyethyleneoxide, and polypropyleneoxide); polyacetals (such as polyoxymethylene); polyamide, polyimide, polyurethane, polyurea, polyesters (such as polyethylene terephthalate and polyethylene naphthalate); polycarbonate, polyketone, polysulfone polyether ketone, phenol resins, melamine resins, cellulose esters (such as diacetylcellulose, triacetylcellulose (TAC), propionylcellulose, butyrylcellulose, acetyl propionylcellulose, and nitrocellulose); polysiloxane, natural polymers (such as cellulose, rubber, and gelatin), and the like.

The polymer substance for use in the present invention is preferably a synthetic polymer, more preferably a polyolefin, an acrylic polymer, polyester, polycarbonate, or a cellulose ester. Among them, polyethylene, polypropylene, poly(4-methylpentene), polymethyl methacrylate, polycarbonate, polyethylene terephthalate, polyethylene naphthalate, polybutylene terephthalate, and triacetylcellulose are particularly preferable.

The polymer substance for use in the present invention is preferably a thermoplastic resin.

The ultraviolet absorbent according to the present invention may be added in any desirable amount for providing desired properties. A smaller content leads to insufficient ultraviolet-shielding effect, while an excessive content to generation of the problem of bleeding out; the favorable content varies according to the compound and the polymer substance used, but is determined properly in experiment by those who are skilled in the art. The content thereof in the polymer material is preferably more than 0 mass % and 20 mass % or less, more preferably more than 0 mass % and 10 mass % or less, and still more preferably 0.05 mass % or more and 5 mass % or less.

The polymer material according to the present invention may contain any additives such as antioxidant, photostabilizer, processing stabilizer, antioxidant, and compatibilizer, as needed in addition to the polymer substance above and the ultraviolet light inhibitor.

The compound according to the present invention is particularly suitable for use in stabilizing an organic material against damage by light, oxygen or heat. In particular, the compound according to the present invention is most suitable for use as a photostabilizer, particularly an ultraviolet absorbent. Hereinafter, application of the compound according to the present invention as an ultraviolet absorbent will be described.

Examples of the materials stabilized by the ultraviolet absorbent according to the present invention include dyes, pigments, foods, beverages, body-care products, vitamins, pharmaceuticals, inks, oils, fats, waxes, surface coating agents, cosmetics, photographic materials, fabrics and the dyes thereof, plastic materials, rubbers, paints, polymer materials, polymer additives and the like.

The ultraviolet absorbent according to the present invention may be used by any method when used. The ultraviolet absorbents according to the present invention may be used alone, or used as a composition, but are preferably used as a composition. In particular, polymer materials containing the ultraviolet absorbent according to the present invention are favorable. Hereinafter, the polymer materials containing the ultraviolet absorbent according to the present invention will be described.

The polymer material containing the ultraviolet absorbent according to the present invention contains a polymer substance. The polymer material containing the ultraviolet absorbent according to the present invention may be a material only of a polymeric substance or a solution of a polymer substance in any solvent.

The polymer material including the ultraviolet absorbent according to the present invention is applicable to any application where synthetic resin is used, and particularly favorably to applications where there is possibility of exposure to light such as sunlight or ultraviolet light. Specific examples thereof include glass alternatives and their surface coating agent; coating agents for the window glass, lighting glass and light-protecting glass such as of house, facility, and vehicle; window films such as of house, facility and vehicle; interior and exterior materials such as of house, facility and vehicle, paints for the interior and exterior materials, and the paint films formed by the paints; alkyd resin lacquer paints and the paint films formed by the paints; acrylic lacquer paints and the paint films formed by the paints; materials for ultraviolet-emission sources such as fluorescent lamp and mercury lamp; materials for precision machines and electric and electronic devices; materials for shielding electromagnetic and other waves emitted from various displays; containers or packaging materials for foods, chemicals and drugs; special packages such as bottle, box, blister, and cup; discoloration inhibitors for compact disk coating, agricultural and industrial sheet or film, print, colored products, dyes and pigments; protective film for polymer supports (e.g., plastic parts such as mechanical and automotive parts); print over-coating, inkjet medium film, delustered laminate film, optical light film, safety glass/front glass intermediate layer, electrochromic/photochromic film, over-lamination film, solar-heat-controlling film, cosmetics such as anti-sunburn cream, shampoo, rinse, and hair dressing; apparel fiber products such as sport wear, stockings and cap and the fibers; home interior products such as curtain, carpet and wall paper; medical devices such as plastic lens, contact lens and artificial eye; optical materials such as optical filter, backlight display film, prism, mirror, and photographic material; mold film, transfer-type sticker, anti-graffiti film, stationery products such as tape and ink; display plates and devices and the surface-coating agents thereof, and the like.

The shape of the polymer material according to the present invention may be flat film, powder, spherical particle, crushed particle, bulky continuous particle, fiber, solenoid, hollow fiber, granule, plate, porous particle, or the other.

The polymer material according to the present invention, which contains the ultraviolet absorbent according to the present invention, is superior in light stability (ultraviolet fastness), causing no precipitation or bleed out of the ultraviolet absorbent during long-term use. In addition, the polymer material according to the present invention, which has superior long-wavelength ultraviolet absorption capacity, can be used as an ultraviolet-absorbing filter or container, for protection, for example, of an ultraviolet-sensitive compound therein. It is possible to obtain a molded article (such as container) of the polymer material according to the present invention, for example, by molding the polymer substance by any molding method such as extrusion molding or injection molding. It is also possible to prepare a molded article having an ultraviolet-absorbing film coated on the polymer material according to the present invention, by coating and drying a solution of the polymer substance on a separately prepared molded article.

When the polymer material according to the present invention is used as an ultraviolet-absorbing filter or film, the polymer substance is preferably transparent. Examples of the transparent polymer materials include cellulose esters (such as diacetylcellulose, triacetylcellulose (TAC), propionylcellulose, butyrylcellulose, acetyl propionyl cellulose, and nitrocellulose), polyamides, polycarbonates, polyesters (such as polyethylene terephthalate, polyethylene naphthalate, polybutylene terephthalate, poly-1,4-cyclohexane dimethylene terephthalate, polyethylene-1,2-diphenoxyethane-4,4'-dicarboxylate, and polybutylene terephthalate), polystyrenes (such as syndiotactic polystyrene), polyolefins (such as polyethylene, polypropylene, and polymethylpentene), polymethyl methacrylate, syndiotactic polystyrene, polysulfones, polyether sulfones, polyether ketones, polyether imides, polyoxyethylene, and the like. Preferable are cellulose esters, polycarbonates, polyesters, polyolefins, and acrylic resins, more preferable are polycarbonates and polyesters, specifically preferable is polyester, and most preferable is polyethylene terephthalate. The polymer material according to the present invention may be used as a transparent support, and the transmittance of the transparent support in such a case is preferably 80% or more, more preferably 86% or more.

In the present invention, two or more kinds of compounds represented by any one of Formulae (1) to (5) different in structure may be used in combination. Alternatively, the compound represented by any one of Formulae (1) to (5) and one or more kinds of ultraviolet absorbents different in structure may be used in combination. Two kinds (preferably three kinds) of ultraviolet absorbents when used in combination absorb ultraviolet ray in a wider wavelength range. In addition, two or more kinds of ultraviolet absorbents, when used in combination, are dispersed more consistently. The ultraviolet absorbent having a structure other than that represented by Formula (1) is not particularly limited. Examples thereof include ultraviolet absorbing structures such as triazine-based, benzotriazole-based, benzophenone-based, merocyanine-based, cyanine-based, dibenzoylmethane-based, cinnamic acid-based, cyanoacrylate-based, and benzoic ester-based compounds. Examples thereof include the ultraviolet absorbents described, for example, in Fine Chemical, May 2004, p. 28 to 38; Survey and Research Dept., Toray Research Center Inc. Ed., "Trend of Functional Additives for Polymers" (Toray Research Center Inc., 1999) p. 96 to 140; and Yasuichi Okatsu Ed., "Development of polymer additives and Environmental Measures" (CMC Publishing, 2003) p. 54 to 64.

Examples of the ultraviolet absorbent having a structure other than that represented by Formula (1) or (6) include compounds such as benzotriazole-based, benzophenone-based, salicylic-acid-based, cyanoacrylate-based, and triazine-based compounds. Particularly preferable are benzotriazole-based compounds.

The effective absorption wavelength of benzotriazole-based compounds is approximately 270 to 380 nm, and specific examples thereof include 2-(2'-hydroxy-5'-methylphenyl)benzotriazole, 2-(2'-hydroxy-5'-t-butylphenyl) benzotriazole, 2-(2'-hydroxy-3'-t-butyl-5'-methylphenyl)-5-chlorobenzotriazole, 2-(2'-hydroxy-3',5'-di-t-butylphenyl)-5-chlorobenzotriazole, 2-(2'-hydroxy-3'-t-butyl-5'-(2-(octyloxycarbonyl)ethyl)phenyl)-5-chlorobenzotriazole, 2-(2'-hydroxy-3'-dodecyl-5'-methylphenyl)-5-chlorobenzotriazole, 2-(2'-hydroxy-3',5'-di-t-amylphenyl)benzotriazole, 2-(2'-hydroxy-5'-t-octylphenyl)benzotriazole, 2-(2'-hydroxy-3',5'-di-(dimethylbenzyl)phenyl)benzotriazole, 2-(2'-hydroxy-4'-octyloxyphenyl)benzotriazole, 2,2'-methylene-bis(2-(2'-hydroxy-5'-t-octylphenyl)benzotriazole)2-(2'-hydroxy-3'-(3,4,5,6-tetrahydrophthalimidylmethyl)-5'-methylbenzyl)phenyl)benzotriazole, and the like.

The effective absorption wavelength of benzophenone-based compounds is approximately 270 to 380 nm, and specific examples thereof include 2,4-dihydroxybenzophenone, 2-hydroxy-4-methoxybenzophenone, 2-hydroxy-4-octyloxybenzophenone, 2-hydroxy-4-decyloxybenzophenone, 2-hydroxy-4-benzyloxybenzophenone, 2-hydroxy-4-(2-hydroxy-3-methacryloxypropoxy)benzophenone, 2-hydroxy-4-methoxy-5-sulfobenzophenone, 2-hydroxy-4-methoxy-5-sulfobenzophenone trihydrate, 2-hydroxy-4-methoxy-2'-carboxybenzophenone, 2-hydroxy-4-octadecyloxybenzophenone, 2-hydroxy-4-diethylamino-2'-hexyloxycarbonylbenzophenone, 2,2'-dihydroxy-4-methoxybenzophenone, 2,2',4,4'-tetrahydroxybenzophenone, 2,2'-dihydroxy-4,4'-dimethoxybenzophenone, 1,4-bis(4-benzyloxy-3-hydroxyphenoxy)butane, and the like.

The effective absorption wavelength of the salicylic acid compounds is approximately 290 to 330 nm, and specific examples thereof include phenyl salicylate, p-t-butylphenyl salicylate, p-octylphenyl salicylate, and the like.

The effective absorption wavelength of cyanoacrylate-based compounds is approximately 270 to 350 nm, and specific examples thereof include 2-ethylhexyl 2-cyano-3,3-diphenylacrylate, ethyl 2-cyano-3,3-diphenylacrylate, hexadecyl 2-cyano-3-(4-methylphenyl)acrylate, salt of 2-cyano-3-(4-methylphenyl)acrylic acid, 1,3-bis(2'-cyano-3,3'-diphenylacryloyl)oxy)-2,2-bis(((2'-cyano-3,3'-diphenylacryloyl)oxy)methyl)propane, and the like.

The effective absorption wavelength of the triazine compounds is approximately 270 to 380 nm, and specific examples thereof include 2-(4-hexyloxy-2-hydroxyphenyl)-4,6-diphenyl-1,3,5-triazine, 2-(4-octyloxy-2-hydroxyphenyl)-4,6-di(2,5-dimethylphenyl)-1,3,5-triazine, 2-(4-butoxy-2-hydroxyphenyl)-4,6-di(4-butoxyphenyl)-1,3,5-triazine, 2-(4-butoxy-2-hydroxyphenyl)-4,6-di(2,4-dibutoxyphenyl)-1,3,5-triazine, 2-(4-(3-(2-ethylhexyloxy)-2-hydroxypropoxy)-2-hydroxyphenyl)-4,6-di(2,4-dimethylphenyl)-1,3,5-triazine, 2-(4-(3-dodecyloxy-2-hydroxypropoxy)-2-hydroxyphenyl)-4,6-di(2,4-dimethylphenyl)-1,3,5-triazine, 2,4-di(4-butoxy-2-hydroxyphenyl)-6-(4-butoxyphenyl)-1,3,5-triazine, 2,4-di(4-butoxy-2-hydroxyphenyl)-6-(2,4-dibutoxyphenyl)-1,3,5-triazine, and the like.

The compound represented by any one of Formulae (1) to (5) may be used favorably as a fluorescent brightener. Generally, fluorescent brighteners are compounds absorbing light at a wavelength of approximately 320 to approximately 410 nm and emitting light at a wavelength of approximately 410 to approximately 500 nm. Fabrics dyed with such a fluorescent brightener gives its inherent yellow reflection light as well as blue light at a wavelength of approximately 410 to approximately 500 nm newly emitted from the fluorescent brightener, giving white reflection light in combination, and increase in visible light energy by fluorescent effect results in increase in whiteness in appearance.

Hereinafter, fluorescent brighteners of the compounds represented by any one of Formulae (1) to (5) will be described. The fluorescent brightener according to the present invention may be used in any form of product. For example, it may be used as a liquid dispersion, a solution, a polymer material, or the like.

The fluorescent brightener according to the present invention may be used as it is dispersed in a dispersion medium. The dispersion medium, preparative process, fluorescent brightener content and dispersion apparatus for the dispersion containing the fluorescent brightener according to the present invention are the same as those for the ultraviolet absorbent described above.

Alternatively, the fluorescent brightener according to the present invention may be used as it is dissolved in a liquid medium. The addition method of the fluorescent brightener according to the present invention to the solution, the content thereof, and the solution are the same as those for the ultraviolet absorbent described above.

The fluorescent brightener according to the present invention is used favorably in a polymer material. The polymer substance, additive, shape, application of the polymer material containing the fluorescent brightener according to the present invention are the same as those described for the ultraviolet absorbent described above.

If the fluorescent brightener according to the present invention does not remove ultraviolet ray in the short-wavelength region sufficiently, an additional ultraviolet absorbent is preferably used.

The ultraviolet absorbent used in combination is not particularly limited. Examples thereof include ultraviolet absorbents represented by any one of Formulae (1) to (5) and those favorable for the ultraviolet absorbent described above. These ultraviolet absorbents may be used alone or in combination of two or more.

The present invention provides a compound for use as an ultraviolet absorbent that improves the ultraviolet durability of a polymer material containing the compound, prevents decomposition of other unstable compounds as the polymer material containing the same is used as an ultraviolet ray filter, and retains its favorable long-wavelength ultraviolet light-absorbing capacity over and extended period.

The compound according to the present invention may be used as a high-light-fastness ultraviolet absorbent. It is also possible to improve the photostability of a polymer molded article such as plastic or fiber, by adding the compound according to the present invention thereto. In addition, the polymer material containing the compound according to the present invention may be used with its superior ultraviolet absorption capacity as a filter or a container for protecting ultraviolet-sensitive products.

The present invention will be described in more detail based on the following examples, but the invention is not intended to be limited thereto.

EXAMPLES

Example 1

Preparation of Exemplary Compound (1)

1.6 g of anthranilic acid was dissolved in 25 ml of cyclohexanone, and 2.5 g of sodium carbonate was added thereto. A solution containing 1.2 g of 2,5-thiophenedicarbonyl dichloride in 4 ml of cyclohexanone was added to the mixture at room temperature. The solution was allowed to react at room temperature for 30 minutes and at 80° C. for 1 hour, and the solid obtained was filtered and washed with water, to give 2.0 g of a synthetic intermediate A (yield: 84%).

(Synthetic intermediate A)

5 ml of acetic anhydride and 5 ml of toluene were added to 1.0 g of the synthetic intermediate A. The mixture was allowed to react under reflux for six hours. After cooled to room temperature, the precipitate was filtered and washed with acetone, to give 0.8 g of an exemplary compound (1) (yield: 88%).

MS: m/z 375 (M+)
$^1$H NMR (CDCl$_3$): δ7.52-7.58 (2H), δ7.67-7.69 (2H), δ7.83-7.88 (2H), δ7.98 (2H), δ8.24-8.26 (2H)
λmax=375 nm (EtOAc)

Example 2

Preparation of Exemplary Compound (1)

1.3 g of anthranilic acid was dissolved in 12 ml of dimethylacetamide, and 1.0 g of 2,5-thiophenedicarbonyl dichloride was added thereto at room temperature. The mixture was allowed to react at room temperature for 1 hour, and the solid obtained was filtered and washed with water, to give 1.8 g of a synthetic intermediate A (yield: 92%).

5 ml of acetic anhydride and 5 ml of toluene were added to 10 g of the synthetic intermediate A. The mixture was allowed to react under reflux for 6 hours. The mixture was cooled to room temperature and filtered, and the resulting solid obtained was washed with acetone, to give 0.8 g of an exemplary compound (1) (yield: 88%).

MS: m/z 375 (M+)
$^1$H NMR (CDCl$_3$): δ7.52-7.58 (2H), δ7.67-7.69 (2H), δ7.83-7.88 (2H), δ7.98 (2H), δ8.24-8.26 (2H)
λmax=375 nm (EtOAc)

Example 3

Preparation of Exemplary Compound (7)

1.6 g of anthranilic acid was dissolved in 25 ml of cyclohexanone, and 2.5 g of sodium carbonate was added thereto. A solution containing 1.2 g of 2,6-pyridinedicarbonyl dichloride in 4 ml of cyclohexanone was added to the mixture at room temperature. The solution was allowed to react at room temperature for 30 minutes and at 80° C. for one hour, and the solid obtained was filtered and washed with water, to give 2.2 g of a synthetic intermediate B (yield: 92%).

(Synthetic intermediate B)

5 ml of acetic anhydride and 5 ml of toluene were added to 1.0 g of the synthetic intermediate B. The mixture was allowed to react under reflux for 10 hours. The mixture was cooled to room temperature and filtered, and the resulting solid obtained was washed with acetone, to give 0.8 g of an exemplary compound (7) (yield: 88%).

MS: m/z 370 (M+)
$^1$H NMR (CDCl$_3$): δ7.61-7.65 (2H), δ7.91-7.92 (4H), δ8.13-8.17 (1H), δ8.31-8.33 (2H), δ8.55-8.57 (2H)
λmax=324 nm (EtOAc)

Example 4

Preparation of Exemplary Compound (8)

2.3 g of oxalyl chloride was added to a mixture of 1.0 g of 2,5-pyridinedicarboxylic acid and 3 ml of toluene. After addition of a few drops of DMF, the mixture was stirred at room temperature for 30 minutes and at 80° C. for 10 minutes. The reaction solution was added to a solution of 1.64 g of anthranilic acid and 4 ml of DMAc, and the solid obtained was filtered and washed with water, to give 2.1 g of a synthetic intermediate C (yield: 88%).

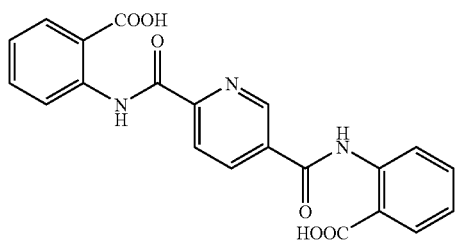
(Synthetic intermediate C)

5 ml of acetic anhydride and 5 ml of toluene were added to 1.0 g of the synthetic intermediate C. The mixture was allowed to react under reflux for 10 hours. The mixture was cooled to room temperature and filtered, and the resulting solid obtained was washed with acetone, to give 0.6 g of an exemplary compound (8) (yield: 66%).

MS: m/z 370 (M+)

$^1$H NMR (CDCl$_3$): δ7.61-7.66 (2H), δ7.79-7.81 (1H), δ7.91-7.93 (3H), δ8.29-8.33 (2H), δ8.52-8.54 (1H), δ8.76-8.79 (1H), δ9.73-9.74 (1H)

λmax=346 nm (EtOAc)

Example 5

Preparation of Exemplary Compound (8)

3.1 g of thionyl chloride was added dropwise to a mixture of 1.0 g of 2,5-pyridinedicarboxylic acid and 3 ml of toluene. A few drops of DMF were added, and the mixture was stirred at 70° C. for 2 hours. The reaction solution was added to a solution of 1.64 g of anthranilic acid in 4 ml of DMAc, and the solid obtained was filtered and washed with water, to give 2.3 g of a synthetic intermediate C (yield: 96%).

5 ml of acetic anhydride and 5 ml of toluene were added to 1.0 g of the synthetic intermediate C. The mixture was allowed to react under reflux for 10 hours. The mixture was cooled to room temperature, and the solid obtained was filtered and washed with acetone, to give 0.6 g of an exemplary compound (8) (yield: 66%).

MS: m/z 370 (M+)

$^1$H NMR (CDCl$_3$): δ7.61-7.66 (2H), δ7.79-7.81 (1H), δ7.91-7.93 (3H), δ8.29-8.33 (2H), δ8.52-8.54 (1H), δ8.76-8.79 (1H), δ9.73-9.74 (1H)

λmax=346 nm (EtOAc)

Example 6

Preparation of Exemplary Compound (21)

10 g of 2-aminobenzamide was dissolved in 50 ml of dimethylacetamide, and 7.7 g of 2,5-thiophenedicarbonyl dichloride was added thereto at room temperature. The mixture was allowed to react at room temperature for 2 hours, and the solid obtained was filtered and washed with water, to give 13.0 g of a synthetic intermediate D (yield: 87%).

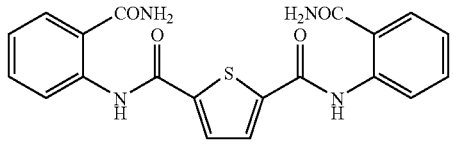
(Synthetic intermediate D)

500 ml of methanol was added to 5.0 g of the synthetic intermediate D. An aqueous solution containing 8 g of cesium carbonate in 30 ml of water was added to the mixture. The mixture was allowed to react at 70° C. for 2 hours. The mixture was cooled to room temperature, then water and hydrochloric acid were added thereto, and the solid obtained was filtered and washed with water acetone, to give 4.0 g of an exemplary compound (21) (yield: 87%).

MS: m/z 372 (M+)

$^1$H NMR (CDCl$_3$): δ7.52-7.56 (2H), δ7.72-7.74 (2H), δ7.84-7.88 (2H), δ8.14-8.16 (2H), δ8.23 (2H), δ12.81 (2H)

λmax=357 nm (EtOAc)

Example 7

Preparation of Exemplary Compound (30)

1.6 g of 4-chloroanthranilic acid was dissolved in 5 ml of dimethylacetamide, and 1.0 g of 2,5-thiophenedicarbonyl dichloride was added thereto at room temperature. The mixture was allowed to react at room temperature for 1 hour; then, 6 ml of acetic anhydride was added; and the mixture was allowed to react under reflux for 6 hours. The mixture was cooled to room temperature, and the solid obtained was filtered and washed with acetone, to give 2.0 g of an exemplary compound (30) (yield: 94%).

MS: m/z 443 (M+)

$^1$H NMR (CDCl$_3$): δ7.49-7.52 (2H), δ7.68-7.69 (2H), δ7.98 (2H), δ8.16-8.18 (2H)

λmax=377 nm (EtOAc)

<Preparation and Evaluation of Sample Solution>

One mg of exemplary compound (1) was dissolved in 100 ml of ethyl acetate, to give a sample solution. Similarly, sample solutions of exemplary compounds (7), (8), (21) and (30) comparative compounds A and B respectively were prepared. The absorbance of each sample solution was determined in a 1 cm quartz cell by using Spectrophotometer UV-3600 (product name) manufactured by Shimadzu Corporation. The cell containing the sample solution was photoirradiated by a xenon lamp with its UV filter removed at an illuminance of 170,000 lux, and the amount of each compound remaining after irradiation for two days was determined. The residual amount was calculated according to the following Formula:

Residual amount(%)=100×(100−Transmittance after irradiation)/(100×Transmittance before irradiation)

The transmittance is a value determined at the maximum absorption wavelength of each compound. The result is shown in Table 7.

TABLE 7

| Sample No. | Compound | Residual amount (%) | |
|---|---|---|---|
| 1 | Exemplified compound (1) | 94 | Present invention |
| 2 | Exemplified compound (7) | 90 | Present invention |
| 3 | Exemplified compound (8) | 91 | Present invention |
| 4 | Exemplified compound (21) | 91 | Present invention |
| 5 | Exemplified compound (30) | 92 | Present invention |
| 6 | Comparative compound A | 83 | Comparative example |
| 7 | Comparative compound B | 27 | Comparative example |

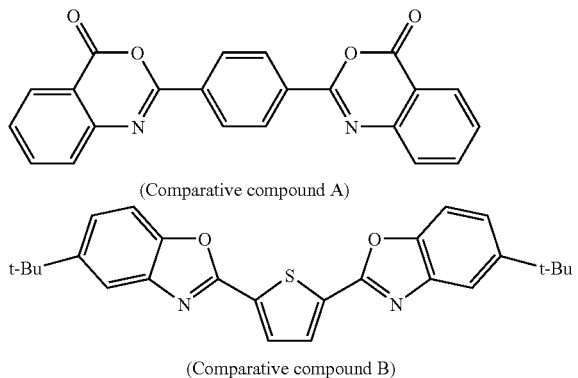

(Comparative compound A)

(Comparative compound B)

As apparent from the results in Table 7, the compounds according to the present invention remained in the sample solution in an amount greater than the comparative compounds A and B (conventional ultraviolet absorbents absorbing light in the UV-A range), indicating that these compounds were more resistant to decomposition by photoirradiation.

Having described our invention as related to the present embodiments, it is our intention that the invention not be limited by any of the details of the description, unless otherwise specified, but rather be construed broadly within its spirit and scope as set out in the accompanying claims.

This non-provisional application claims priority under 35 U.S.C. §119 (a) on Patent Application No. 2007-095435 filed in Japan on Mar. 30, 2007 and Patent Application No. 2008-021824 filed in Japan on Jan. 31, 2008, each of which is entirely herein incorporated by reference.

What we claim is:

1. A compound represented by the following Formula (4):

Formula (4)

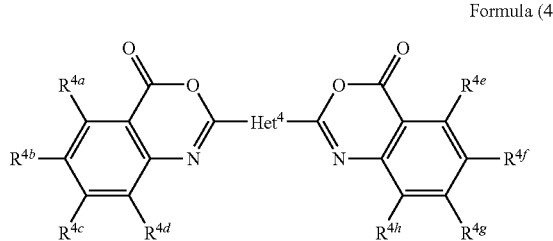

wherein, $Het^4$ represents a bivalent five- or six-membered aromatic heterocyclic residue derived from a compound selected from the group consisting of pyrrole, pyrazole, imidazole, 1,2,3-triazole, 1,2,4-triazole, pyridine, pyridazine, pyrimidine, pyrazine, 1,3,5-triazine, furan, thiophene, oxazole, isoxazole, thiazole, isothiazole, 1,2,3-oxadiazole, and 1,3,4-thiadiazole; the aromatic heterocyclic residue may further be substituted wherein the substituent is selected from the group consisting of a halogen atom, an alkyl group having 1 to 20 carbon atoms, an aryl group having 6 to 20 carbon atoms, a cyano group, a carboxyl group, an alkoxycarbonyl group, an aryloxycarbonyl group, a substituted or unsubstituted carbamoyl group, an alkylcarbonyl group, an arylcarbonyl group, a nitro group, a substituted or unsubstituted amino group, an acylamino group, a sulfonamido group, an imido group, an imino group, a hydroxy group, an alkoxy group having 1 to 20 carbon atoms, an aryloxy group, an acyloxy group, an alkylsulfonyloxy group, an arylsulfonyloxy group, a sulfo group, a substituted or unsubstituted sulfamoyl group, an alkylthio group, an arylthio group, an alkylsulfonyl group, an arylsulfonyl group, and a heterocyclic group having 6 to 20 carbon atoms; $R^{4a}$, $R^{4b}$, $R^{4c}$, $R^{4d}$, $R^{4e}$, $R^{4f}$, $R^{4g}$ and $R^{4h}$ each independently represent a hydrogen atom or a monovalent substituent group wherein the substituent group is selected from the group consisting of a halogen atom, an alkyl group having 1 to 20 carbon atoms, an aryl group having 6 to 20 carbon atoms, a cyano group, a carboxyl group, an alkoxycarbonyl group, an aryloxycarbonyl group, a substituted or unsubstituted carbamoyl group, an alkylcarbonyl group, an arylcarbonyl group, a nitro group, a substituted or unsubstituted amino group, an acylamino group, a sulfonamido group, an imido group, an imino group, a hydroxy group, an alkoxy group having 1 to 20 carbon atoms, an acyloxy group, an alkylsulfonyloxy group, an arylsulfonyloxy group, a sulfo group, a substituted or unsubstituted sulfamoyl group, an alkylthio group, an arylthio group, an alkylsulfonyl group, an arylsulfonyl group, and a heterocyclic group having 6 to 20 carbon atoms.

2. The compound according to claim 1, wherein the compound represented by Formula (4) above is a compound represented by the following Formula (5):

Formula (5)

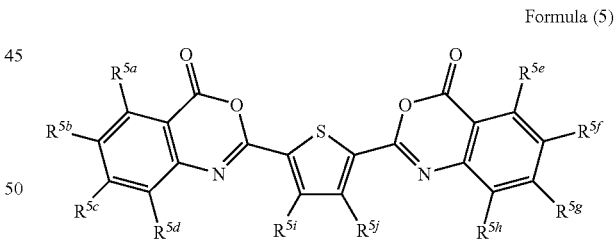

wherein, $R^{5a}$, $R^{5b}$, $R^{5c}$, $R^{5d}$, $R^{5e}$, $R^{5f}$, $R^{5g}$ and $R^{5h}$ each are the same as $R^{4a}$, $R^{4b}$, $R^{4c}$, $R^{4d}$, $R^{4e}$, $R^{4f}$, $R^{4g}$ and $R^{4h}$ in Formula (4) above; $R^{5i}$ and $R^{5j}$ each independently represent a hydrogen atom or a monovalent substituent group.

* * * * *